(12) United States Patent
Xu et al.

(10) Patent No.: US 8,937,509 B2
(45) Date of Patent: Jan. 20, 2015

(54) MULTI-CHANNEL BIOPOTENTIAL SIGNAL ACQUISITION SYSTEMS

(75) Inventors: Jiawei Xu, Eindhoven (NL); Refet Firat Yazicioglu, Leuven (BE)

(73) Assignees: IMEC, Leuven (BE); Stichting IMEC Nederland, Eindhoven (NL)

( * ) Notice: Subject to any disclaimer, the term of this patent is extended or adjusted under 35 U.S.C. 154(b) by 673 days.

(21) Appl. No.: 13/227,316

(22) Filed: Sep. 7, 2011

(65) Prior Publication Data

US 2012/0095361 A1    Apr. 19, 2012

Related U.S. Application Data

(60) Provisional application No. 61/393,602, filed on Oct. 15, 2010.

(30) Foreign Application Priority Data

Feb. 18, 2011  (EP) .................................... 11155072

(51) Int. Cl.
*H03F 3/45* (2006.01)
*A61B 5/05* (2006.01)

(52) U.S. Cl.
USPC ......... 330/258; 330/295; 330/260; 330/124 R

(58) Field of Classification Search
USPC ............... 330/258, 295, 260, 124 R; 600/547
IPC ....................... H03F 3/45; A61B 5/05
See application file for complete search history.

(56) References Cited

U.S. PATENT DOCUMENTS

| | | | |
|---|---|---|---|
| 3,955,149 A * | 5/1976 | Trilling .......................... | 330/258 |
| 4,289,142 A | 9/1981 | Kearns | |
| 5,206,602 A * | 4/1993 | Baumgartner et al. ........... | 330/9 |
| 5,226,425 A * | 7/1993 | Righter .......................... | 600/523 |
| 5,392,784 A | 2/1995 | Gudaitis | |
| 5,713,365 A | 2/1998 | Castelli | |
| 6,438,406 B2 | 8/2002 | Yonce | |
| 7,148,701 B2 * | 12/2006 | Park et al. ...................... | 324/629 |

(Continued)

FOREIGN PATENT DOCUMENTS

| | | |
|---|---|---|
| EP | 0012530 | 8/1980 |
| WO | WO 2009/017413 A1 | 2/2009 |

OTHER PUBLICATIONS

Verma et al., "A Micro-Power EEG Acquisition SoC With Integrated Feature Extraction Processor for a Chronic Seizure Detection System", IEEE Journal of Solid-State Circuits, vol. 45, No. 4, Apr. 2010, pp. 804-816.

(Continued)

*Primary Examiner* — Patricia Nguyen
(74) *Attorney, Agent, or Firm* — Knobbe Martens Olson & Bear LLP

(57) ABSTRACT

A multi-channel biopotential signal acquisition system is disclosed. In the system, a plurality of biopotential channels is corrected for common-mode interference. In one aspect, each biopotential channel includes an electrode for providing a biopotential input signal and an associated amplifier for amplifying the biopotential input signal and providing a biopotential output signal. The output signal is processed in a processor. Each biopotential output signal is passed to a common-mode feedback system, which determines an average common-mode signal and feeds that signal back to each of the amplifiers in each of the biopotential channels to enhance common-mode rejection ratio of the system.

18 Claims, 12 Drawing Sheets

(56) References Cited

U.S. PATENT DOCUMENTS

| | | | |
|---|---|---|---|
| 7,991,359 B2* | 8/2011 | Tamura | 455/63.1 |
| 2010/0094147 A1 | 4/2010 | Inan et al. | |
| 2010/0106041 A1* | 4/2010 | Ghovanloo et al. | 600/544 |
| 2010/0145217 A1* | 6/2010 | Otto et al. | 600/544 |

OTHER PUBLICATIONS

Fernández et al., "A Simple Active Electrode for Power Line Interference Reduction In High Resolution Biopotential Measurements", 18$^{TH}$ Annual International Conference of the IEEE Engineering in Medicine and Biology Society, Amsterdam 1996 1.2.3: Bioelectrodes I, vol. 1, pp. 97-98.

Galjan et al., "Highly Sensitive Biomedical Amplifier With Cmrr Calibration and Dc-Offset Compensation", 2009 IEEE, pp. 152-155.

Grimbergen et al., "High-quality recording of bioelectric events—Part 1 Interference reduction, theory and practice", Medical & Biological Engineering & Computing, Sep. 1990, pp. 389-397.

Spinelli et al., "A Transconductance Driven-Right-Leg Circuit", IEEE Transactions on Biomedical Engineering, vol. 46, No. 12, Dec. 1999, pp. 1466-1470.

Extended European Search Report for European Patent Application No. 11155072.9-2319 dated May 16, 2011.

Rahal et al., "An Integrated Common-Mode Feedback Topology for Multi-Frequency Bioimpedance Imaging", IEEE Conference 35$^{th}$ European Solid-State Circuits Conference (ESSCIRC), 2009, pp. 417-420.

Rosell et al., "Common-mode feedback in electrical impedance tomography", Clin. Phys. Physiol. Meas., 1992, vol. 13, Suppl. A, 11-14.

Winter et al. "Driven-Right-Leg Circuit Design", IEEE Transactions on Biomedical Engineering, vol. BME-30, No. 1, Jan. 1983, pp. 62-66.

Degen et al., "Enhancing interference rejection of preamplified electrodes by automated gain adaption", IEEE Transactions on Biomedical Engineering, 2004.

W.H. Ko, "Active electrodes for EEG and evoked potential", Proceedings of the 20$^{th}$ Annual International Conference of the IEEE Engineering in Medicine and Biology Society, vol. 20, No. 4, 1998, pp. 2221-2224.

Fan et al., "A 1.8µW 1µV-Offset Capacitively-Coupled Chopper Instrumentation Amplifier in 65nm CMOS", IEEE ESSCIRC 2010.

Denison et al., "A 2.2µW 94nV/√Hz, Chopper-Stabilized Instrumentation Amplifier for EEG Detection in Chronic Implants", ISSCC Dig. Tech. Papers, 2007, pp. 162-594.

Yazicioglu et al., "A 60µW 60nV/√Hz Readout Front-End for Portable Biopotential Acquisition Systems", IEEE J. Solid-State Circuits, May 2007, pp. 1100-1110.

Zou et al., "A 1-V 450-nW Fully Integrated Programmable Biomedical Sensor Interface Chip", IEEE J. Solid-State Circuits, Apr. 2009, pp. 1067-1077.

Wu et al., "A Chopper Current-Feedback Instrumentation Amplifier With a 1 mHz 1/F Noise Corner and an AC-Coupled Ripple Reduction Loop" IEEE J. Solid-State Circuits, Dec. 2009, pp. 3232-3243.

* cited by examiner

MULTI-CHANNEL BIOPOTENTIAL SIGNAL ACQUISITION SYSTEMS

CROSS REFERENCE TO RELATED APPLICATIONS

This application claims priority under 35 U.S.C. §119(e) to U.S. provisional patent application 61/393,602 filed on Oct. 15, 2010, which application is hereby incorporated by reference in its entirety.

BACKGROUND OF THE INVENTION

1. Field of the Invention

The disclosed technology relates to multi-channel biopotential signal acquisition systems and, more particularly, to active electrode based systems that comprise enhanced common-mode rejection ratio techniques.

2. Description of the Related Technology

Active electrodes have been employed where electrodes are integrated with amplifiers for the suppression of interference picked up from cables. An ideal active electrode comprises a passive electrode and a pre-amplifier that are co-integrated in the same package which can be placed very close to the skin to extract low-level biopotential signals. In this way, the signal path length between the electrode and the pre-amplifier is minimized, maintain the highest possible input impedance of the amplifier. Furthermore, the output of the active electrode forming a low-impedance node and the interference and motion artifacts obtained by cable movement and electromagnetic fields in the vicinity can both be reduced when compared to a conventional passive electrode interface where a high impedance node between the electrode and the amplifier picks up interference currents.

Common mode (CM) interference is one of the major problems in such active electrode biopotential signal acquisition systems. CM interference at inputs of the active electrode can be converted to a differential mode (DM) error at the outputs of the active electrode pairs due to the voltage gain mismatch between these active electrode pairs. The output error can have significant large amplitude when compared to the amplitude of the biopotential signals. As a result, in multi-channel biopotential acquisition systems, it is necessary to have good common-mode rejection ratio (CMRR) to reject 50 Hz or 60 Hz CM interferences whilst extracting µV level biopotential signals.

State-of-the-art active electrode systems employ voltage buffers to achieve good CMRR between electrode pairs. One such active electrode is described in "A Simple Active Electrode for Power Line Interference Reduction in High Resolution Biopotential Measurements" by M. Fernandez and R. Pallas-Areny, Proc. 18$^{th}$ Annual International Conference, IEEE Engineering in Medicine and Biology Society, vol. 1, pages 97 to 98, 1997. In this active electrode, a voltage buffer is used to facilitate inter-channel gain matching that is necessary to achieve a high CMRR. However, low noise buffers consume significant power and, due to their lack of gain, still require the use of a back-end that is low noise and power hungry to maintain the total integrated noise at acceptable levels.

An amplifier with gain can effectively reduce the power consumption from the back-end processor whilst achieving the same input referred noise of the system. However, gain mismatch between electrode pairs usually limits the CMRR to between 60 dB and 70 dB. One design is described in "A Micro-Power EEG Acquisition SoC with Integrated Feature Extraction Processor for a Chronic Seizure Detection System by N. Verma, A. Shoeb, A. J. Bohorquez et al, IEEE J. Solid-State Circuits, pages 804 to 816, April 2010, where the CMRR is limited to 60 dB by capacitor mismatch.

Common-mode feedback (CMFB) has been found to be a solution for reducing effective CM interferences and improving CMRR between amplifier pairs. Such a method is described in "Highly Sensitive Biomedical Amplifier with CMRR Calibration and DC-Offset Compensation" by W. Galjan, K. M. Hafkemeyer, J. M. Tomasik, F. Wagner, W. H. Krautschneider and D. Schroeder, EUROCON2009. Here, a known CM input is applied during calibration where the output DM error voltage is sensed, digitized and fed back to adjust a resistive digital-to-analogue converter (DAC) so that the voltage gain of the amplifier pairs can be matched. During amplification, amplifiers, for which the gain has been calibrated, amplify the biopotential signals with enhanced CMRR. However, calibration for a multi-channel system disturbs continuous-time monitoring.

A continuous-time CMRR enhancement method employing CMFB is described in "High Quality Recording of Bioelectric Events I: Interference Reduction, Theory and Practice" by C. A. Grimbergen, A. C. Metting Van Rijn and A. Peper, EMBC 1990. A circuit, used in such a method, is known as a driven-right-leg (DRL) circuit. An output CM sensing circuit is used and the output CM voltage is fed back to the patient by way of a reference electrode. The CMFB circuit can reduce the effect of CM gain and therefore improves CMRR.

However, DRL circuits suffer from stability problems and require large power dissipation as the CM signal is fed back through the reference electrode with significant large impedance described in "A Transconductance Driven-Right-Leg Circuit" by E. M. Spinelli et al., IEEE Transaction on Biomedical Engineering, Vol. 46, No. 12, pages 1466 to 1470, December 1999.

SUMMARY OF CERTAIN INVENTIVE ASPECTS

Certain inventive aspects relate to a active electrode based multi-channel biopotential signal acquisition system that has continuous-time CMRR improvement.

In accordance with one inventive aspect, there is provided a biopotential signal acquisition system for acquiring biopotential signals of a user, the system comprising:—at least two biopotential channels, each channel including an electrode for detecting a biopotential input signal and an amplifier for amplifying the biopotential input signal to provide an amplified biopotential output signal, at least one of the biopotential channels comprising an active electrode formed by the electrode and the amplifier; a back-end processing circuit for processing the amplified biopotential output signals; and a common-mode feedback system connected to receive the amplified biopotential output signals to determine an average common-mode signal from the amplified biopotential output signals, and for feeding the average common-mode signal back to each amplifier to enhance common-mode rejection ratio of the system.

In one inventive aspect, each amplifier that amplifies the detected biopotential input signal has gain.

In one inventive aspect, the average output common-mode voltage is sensed and fed back to the active electrodes, thus the effective common-mode gain of active electrode is reduced for CMRR enhancement.

In one inventive aspect, the CMRR enhancement technique operates in continuous-time mode without interrupting biopotential signal monitoring. Moreover, the use of a reference electrode can be eliminated and common average montage can be implemented that simplifies the design of the CMFB circuit as the stability of conventional DRL circuits significantly suffers from the impedance of the reference electrode.

By using active electrodes with gain the low noise requirement from the back-end is reduced, thereby reducing the overall power consumption of the system.

In a multi-channel system, a plurality of biopotential channels are provided, each biopotential channel including an active electrode, the average common-mode signal being fed back to an input of each amplifier.

In one inventive aspect, the common-mode feedback system comprises an inverting common-mode feedback system and each active electrode comprises an inverting amplifier. In this case, the average common-mode signal is fed back to the non-inverting input of the amplifier. Here, the inverting common-mode feedback system may comprise a capacitive summing amplifier.

In one inventive aspect, the common-mode feedback system comprises a non-inverting common-mode feedback system and each active electrode comprises a non-inverting amplifier. In this case, the common-mode signal is fed back to the inverting input of the amplifier. Here, the non-inverting common-mode feedback system may comprise an open-loop voltage summing amplifier.

Additionally, each active electrode may include one or more of: an impedance boost loop, a ripple reduction loop, and a DC servo loop.

In one inventive aspect, the common-mode feedback system forms part of the back-end processor, and each amplifier in each active electrode comprises a chopper-stabilized capacitively-coupled amplifier. In addition, the back-end processing circuit may comprise a further amplifier and an analogue-to-digital converter. In an embodiment, the common-mode feedback system comprises a back-end capacitive summing amplifier thereby providing enough CMFB gain for CMRR enhancement, providing AC coupling characteristic to reject active electrode offset thus avoid saturation of the back-end summing amplifier and providing capacitive load impedance for at least two active electrodes.

One inventive aspect improves the gain mismatch and CMRR of the active electrodes, thereby allowing a power efficient back-end to be used which reduces the total power dissipation of the system.

BRIEF DESCRIPTION OF THE DRAWINGS

For a better understanding of the present invention, reference will now be made, by way of example only, to the accompanying drawings in which.

DETAILED DESCRIPTION OF CERTAIN ILLUSTRATIVE EMBODIMENTS

Figure 1:
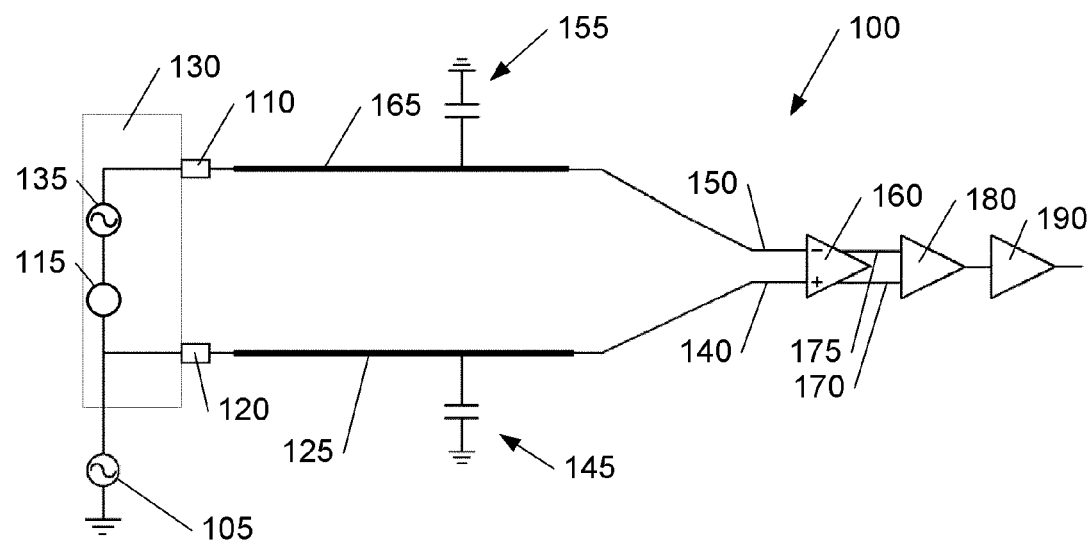
FIG. 1 is a schematic illustration of a conventional biopotential acquisition system having a passive electrode arrangement.

The present invention will be described with respect to particular embodiments and with reference to certain drawings but the invention is not limited thereto. The drawings described are only schematic and are non-limiting. In the drawings, the size of some of the elements may be exaggerated and not drawn on scale for illustrative purposes.

Components that are identical are referenced the same in each Figure of the drawings.

Referring initially to FIG. 1, a conventional passive biopotential acquisition system 100 is shown. The system 100 comprises a first passive electrode 110 and a second passive electrode 120 that are positioned in contact with skin 130 of a patient whose biopotential signals 135 are to be acquired. Each electrode 110, 120 is connected to respective inverting and non-inverting inputs 140, 150 of and instrumentation amplifier (IA) 160. Outputs 170, 175 are applied to a programmable gain amplifier (PGA) 180. The output of the PGA 180 is passed to an analogue-to-digital converter (ADC) 190. CM interference and electrode offset (EO) are indicated by 105, 115 as shown.

In FIG. 1, there are high input impedance nodes and the system 100 is sensitive to cable artifacts as well as input stray capacitances, illustrated by capacitors 145, 155 attached to connections between the electrodes 110, 120 and the IA 160. These connections are provided by expensive low-noise heavy coaxial cables 125, 165.

Figure 2:
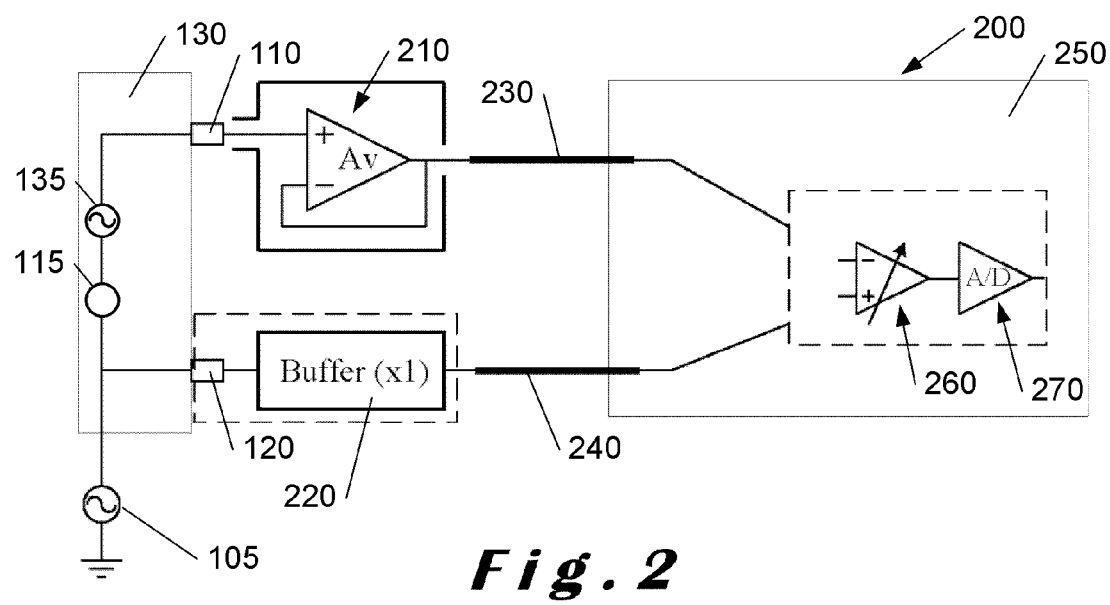
FIG. 2 is a schematic illustration of a conventional biopotential acquisition system having an active electrode arrangement.

FIG. 2 illustrates a conventional active electrode biopotential acquisition system 200. As described with reference to FIG. 1, electrodes 110, 120 are connected to skin 130 of a patient. In this case, the first electrode 110 is connected to a first voltage buffer 210 and the second electrode 120 is connected to a second voltage buffer 220. The first electrode 110 and the first voltage buffer 210 and the second electrode 120 and the second voltage buffer 220 form two active electrodes. Cables 230, 240 connect respective ones of the first and second buffers 210, 220 to a back-end 250. In the back-end 250, a variable gain amplifier (VGA) 260 is connected to ends of the cables 230, 240 and provides an input for an ADC 270. CM interference, electrode offset and the biopotential signal are indicated by 105, 115, 135 respectively as before.

Buffers 210, 220 are typically implemented as unity-gain voltage buffers which does not provide any amplification but adds noise to the signal. Therefore, the use of such buffers still requires a low-noise and hence power hungry amplifier 260 in the back-end, thereby adding to the power consumption of the system 200. In order to reduce the power consumption of a back-end, an active electrode with gain can be used.

Figure 3:
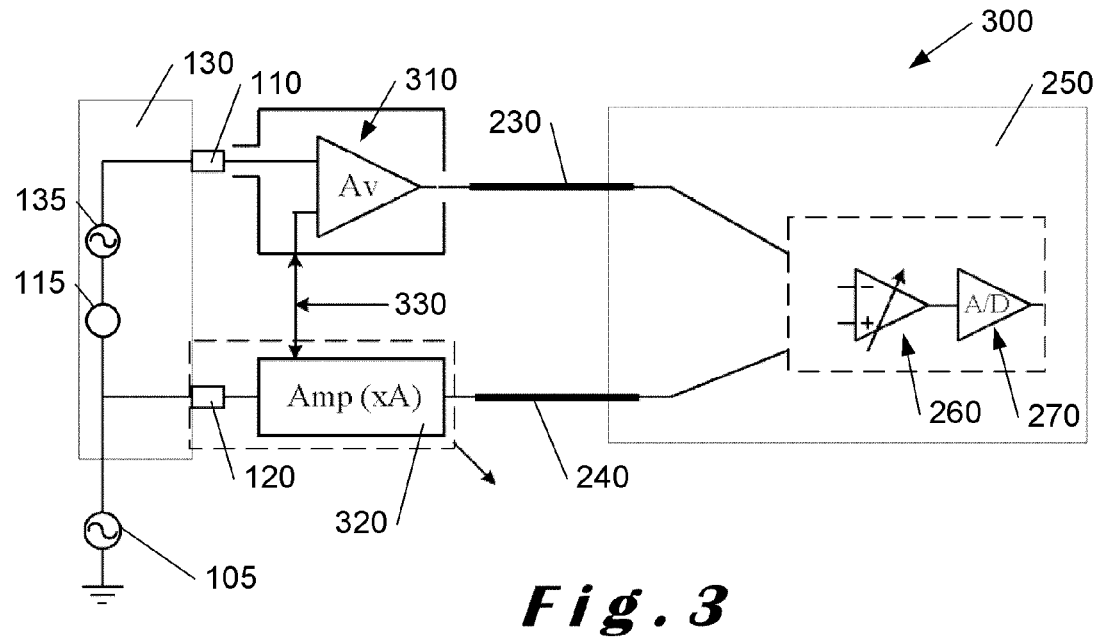
FIG. 3 is a schematic illustration of a biopotential acquisition system in accordance with one embodiment.

In FIG. 3, a conventional active electrode biopotential acquisition system 300 is shown that utilizes an active electrode with gain. As before, electrodes 110, 120 are connected to the skin 130 of a patient and the CM interference, electrode offset and the biopotential signal are indicated by 105, 115, 135 respectively. Electrodes 110, 120 are connected to respective ones of a first amplifier 310 and a second amplifier 320. Electrode 110 and amplifier 310 together form a first active electrode and electrode 120 and amplifier 320 together form a second active electrode. Cables 230, 240 connect respective ones of the amplifiers 310, 320 to the back-end 250 as before. A voltage reference signal 330 is applied to both amplifiers 310, 320 as shown. However, the gain mismatch between the amplifier pair 310, 320 will limit the CMRR of the system 300.

Figure 4:
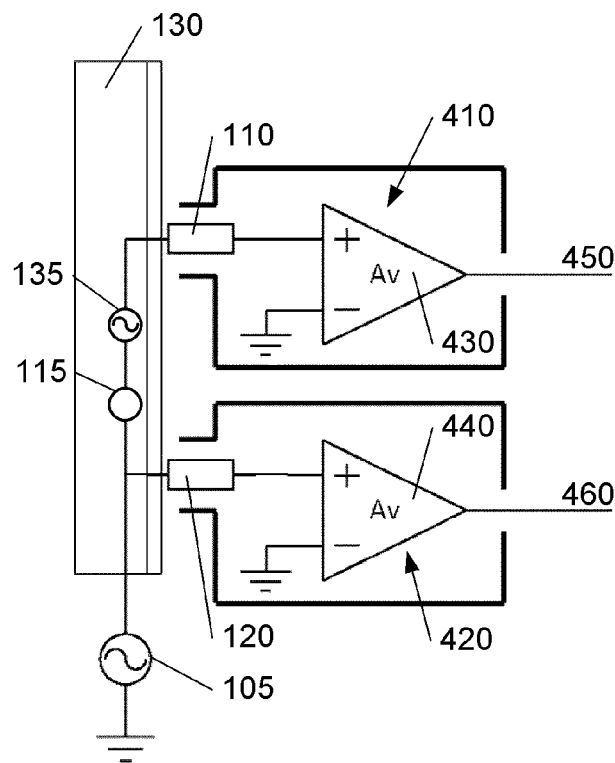
FIG. 4 is a schematic illustration of a conventional biopotential acquisition system having a differential output error voltage due to gain mismatch.

FIG. 4 illustrates CM interference being converted to a DM error at the output due to the gain mismatch between active electrode pairs as discussed above. Two active electrodes 410, 420 are shown that comprise respective electrodes 110, 120 and amplifiers 430, 440. The voltage gain for the first active electrode 410 is Av and provides an output signal 450. The voltage gain for the second active electrode 420 is Av+Δ and provides an output signal 460. The difference, Δ, is due to CM interference 105 that has been converted to a DM error at the output. Output signals 450, 460 are therefore different.

Figure 5:
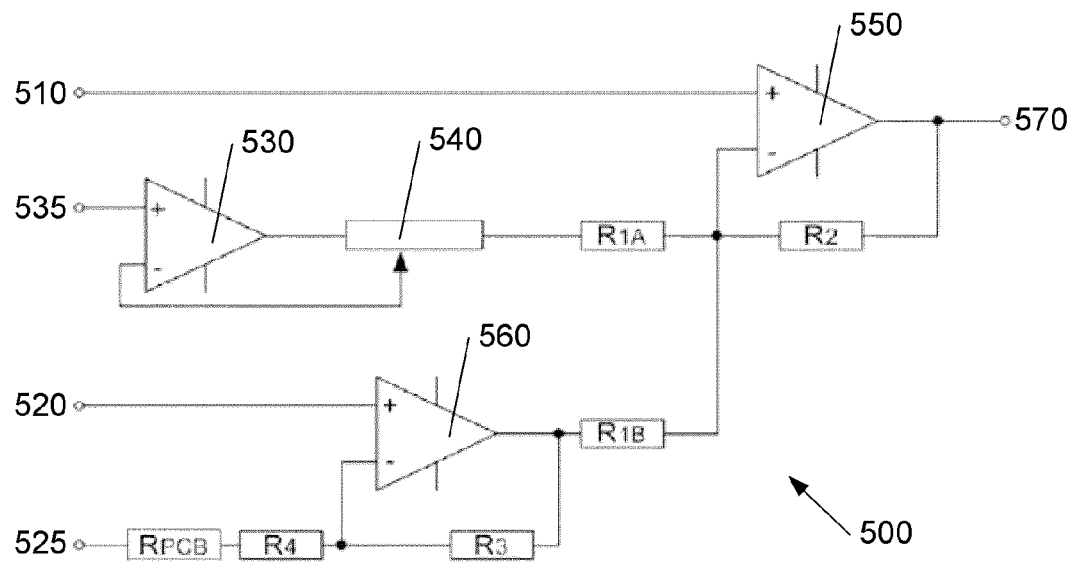
FIG. 5 is a schematic illustration of a conventional biopotential acquisition system using CMFB and CMRR calibration.

FIG. 5 illustrates a CMFB calibration technique as discussed above with reference to the article by W. Gljan, K. M. Hafkemeyer, J. M. Tomasik, F. Wagner, W. H. Krautschneider and D. Schroeder. A calibration system 500 is shown in which a sensor signal 510 from a first electrode and a reference signal 520 from a second electrode are input. CMRR calibration is carried out using an operational amplifier (OPAMP) 530 connected to receive a DAC input 535 at its non-inverting input. The inverting input to the OPAMP 530 is used for calibration in a calibration arrangement 540. Both the sensor signal 510 and the reference signal 520 are input to the non-inverting inputs of respective amplifiers 550, 560 as shown. The inverting input of amplifier 560 is connected to ground 525 and the inverting input of amplifier 550 receives the calibrated output of the calibration arrangement 540. A single output signal 570 is provided from the calibration system as shown. The gain of amplifier 550 has been calibrated by the calibration arrangement 540 and the amplifier 550 will amplify the biopotential signals with enhanced CMRR.

Figure 6:
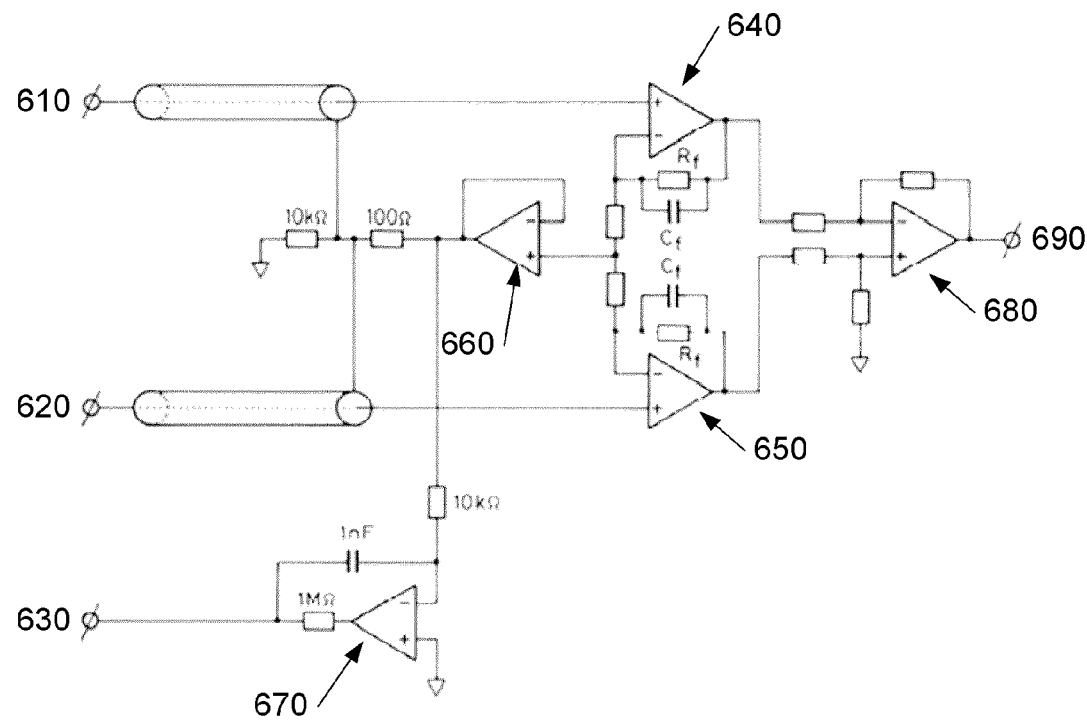
FIG. 6 is a schematic illustration of a conventional biopotential acquisition system using continuous-time CMRR with a DRL circuit.

A DRL circuit 600 is shown in FIG. 6 as described in the article "High Quality Recording of Bioelectric Events I: Interference Reduction, Theory and Practice" discussed above. In the circuit 600, two input signals 610, 620 are provided as well as a driven-right-leg 630. Various amplifiers 640, 650, 660, 670, 680 are used in the circuit with an output 690 being provided by amplifier 680.

Figure 7:
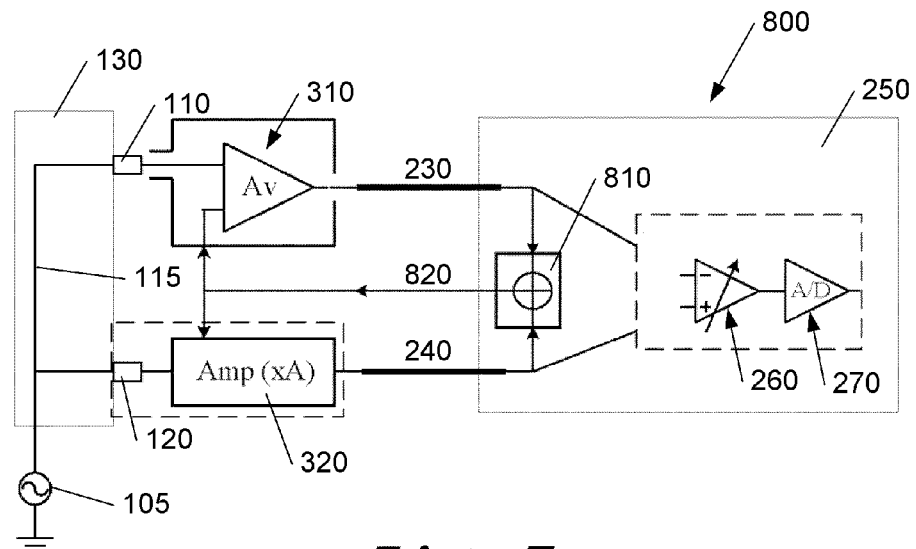
FIG. 7 is a detailed schematic illustration of a biopotential acquisition.

In FIG. 7, a CMFB circuit 800 for CMRR improvement of the two active electrode system is shown. The circuit 800 is similar to the circuit 300 of FIG. 3 but with the reference voltage signal 330 replaced with a CMFB signal 820 generated by a summing amplifier 810. (Components that are identical to those described in FIG. 3 are not discussed again here.) The CM output signals of active electrodes 310, 320 are summed, amplified and fed back as correction signals for each of the amplifiers 310, 320. In one embodiment, the CMFB system 810 comprises a summing amplifier but any other system arranged for generating an average CM signal known in the art can be used. Other examples of such system for generating an average CM signal include: a resistive CM detector; a switched-capacitor CM detector; a triode transistor CM detector; and a differential transistor CM detector. Although only two channels are shown in FIG. 7, it will be appreciated that a CMFB circuit can be extended for use with many channels.

Figure 8:
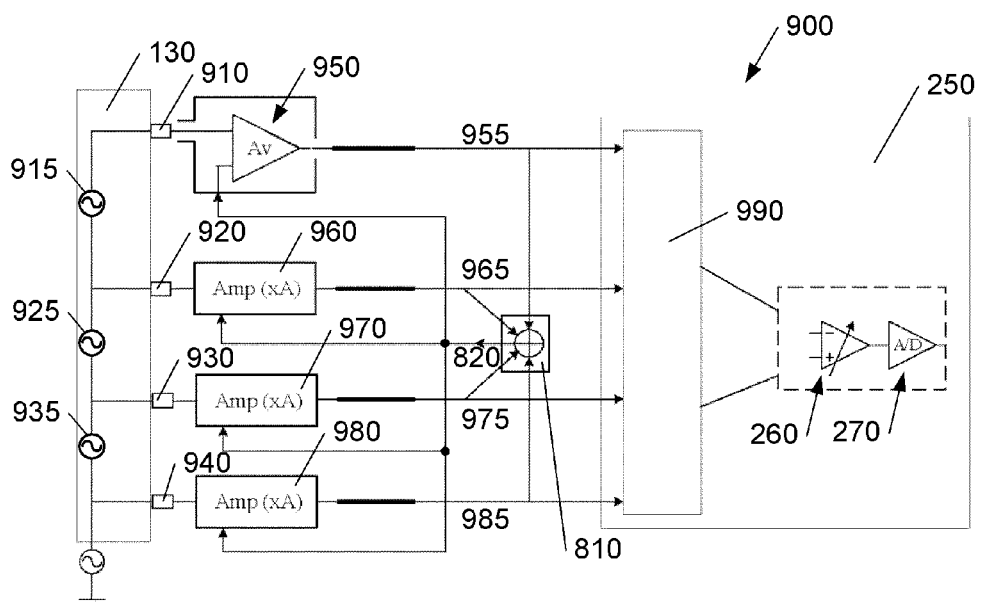
FIG. 8 is more detailed illustration of the system of FIG. 7 for multiple channels.

In FIG. 8, a multi-channel CMFB circuit 900 for CMRR improvement is shown. In this case, four channels are shown where four electrodes 910, 920, 930, 940 are applied to the skin 130 of a patient. Biopotential signals between electrodes 910, 920, 930, 940 are indicated as 915, 925 and 935 respectively. Amplifiers 950, 960, 970, 980 are provided for amplifying the signals received by respective ones of the electrodes 910, 920, 930, 940 and for providing output signals along cables 955, 965, 975, 985 to the back-end 250. Active electrodes are formed by electrode 910, 920, 930, 940 and their associated amplifiers 960, 970, 980. As before, signals that are being passed to the back-end 250 are applied to the CMFB system 810 where the CMFB signal 820 is generated and output as correction signals for each of the amplifiers 950, 960, 970, 980. The back-end 250 includes a multiplexer 990 for receiving the signals from the cables 955, 965, 975, 985 and for controlling their passing through to the VGA 260 and ADC 270 for subsequent processing.

The amplifier embedded in each active electrode shown in FIGS. 7 and 8 can be implemented as an inverting amplifier or a non-inverting amplifier. In order to maintain a negative feedback for system stability, the back-end CMFB circuit can therefore be implemented as an inverting amplifier or a non-inverting amplifier respectively. This is described below with reference to FIGS. 9 to 14. Moreover, the biopotential acquisition system of one embodiment will be described with reference to an eight-channel active electrode amplifying system for EEG monitoring but is not limited hereto.

Figure 9:
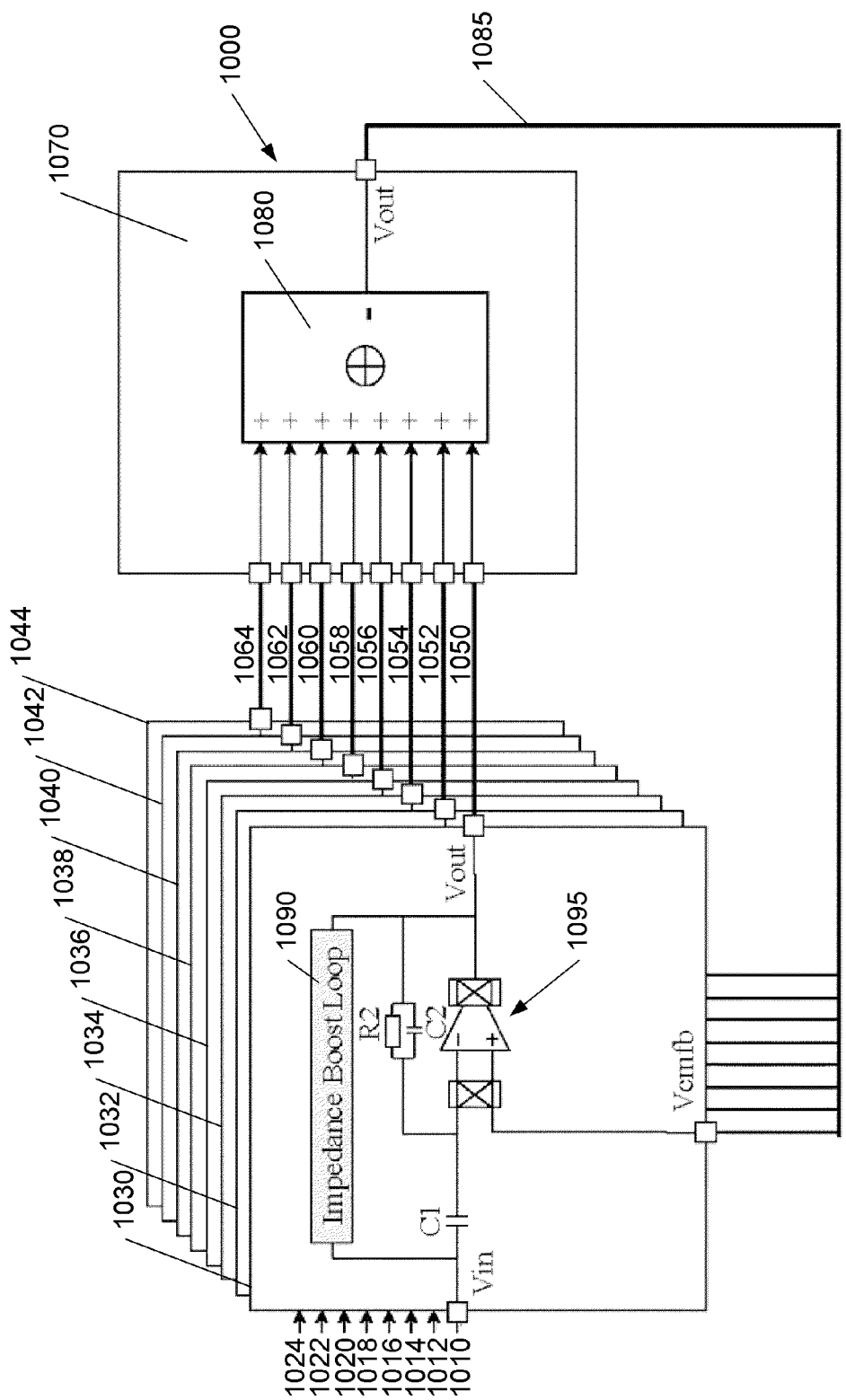
FIG. 9 is similar to FIG. 8 but for a system having an inverting amplifier and inverting CMFB circuit.

FIG. 9 illustrates an eight-channel active electrode system 1000 with inverting amplifier and inverting CMFB. Eight input channels 1010, 1012, 1014, 1016, 1018, 1020, 1022, 1024 are input to respective active electrodes 1030, 1032, 1034, 1036, 1038, 1040, 1042, 1044 as shown. Each active electrode is based on a chopper-stabilized amplifier with selectable gain. Eight output signals 1050, 1052, 1054, 1056, 1058, 1060, 1062, 1064 from respective ones of the active electrodes 1030, 1032, 1034, 1036, 1038, 1040, 1042, 1044 are input to a back-end 1070. The back-end 1070 comprises an inverting CMFB circuit 1080 that provides an output 1085 that is fed back to each of the active electrodes 1030, 1032, 1034, 1036, 1038, 1040, 1042, 1044 as shown. This improves the CMRR between electrode pairs which would otherwise be limited by gain mismatch by feeding the average output CM voltage of all eight amplifiers, in output 1085, back to their non-inverting inputs as shown. This reduces the effective CM voltage applied to each amplifier and thus boosts the CMRR between electrode pairs by 20 log(Av), where Av is the nominal voltage gain of each electrode. This can be compared to the traditional DRL circuit as discussed above, which can also be used to improve the CMRR of active electrodes. However, as mentioned above, DRL circuits suffer from stability problems and increased power dissipation, since the CM signal must be feed back through an electrode with significant impedance.

Figure 10:
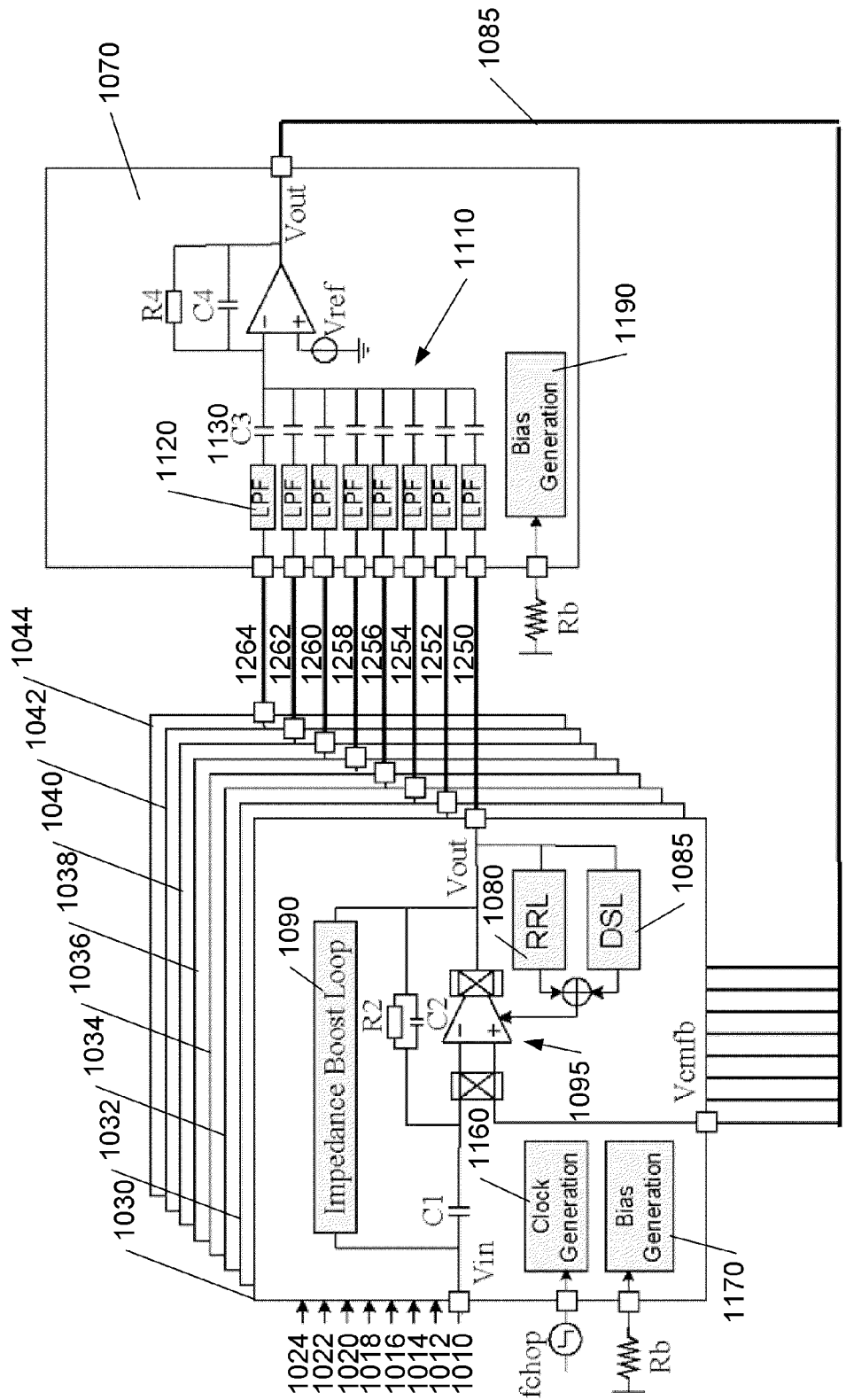
FIG. 10 is similar to FIG. 9 but illustrating a possible implementation of the inverting CMFB circuit.

Each active electrode 1030, 1032, 1034, 1036, 1038, 1040, 1042, 1044 comprises an impedance boost circuit 1090 with an inverting amplifier arrangement 1095 and two calibration loops that improve the input impedance as well as provide compensation for the offset of the amplifier as shown in FIG. 10. The impedance boost circuit 1090 will be described in more detail below.

The mid-band gain of the amplifier, $A_v$, can be expressed as:

$$A_v = \frac{C_2}{C_1}$$

where $C_1$ and $C_2$ are respectively the capacitance values of the AC coupling capacitor and feedback capacitors as shown in FIG. 10. It will be appreciated that different gains can be obtained by changing the value of $C_2$. The AC coupling capacitor effectively rejects any EO whilst pseudo-resistor $R_2$ and the capacitor $C_2$ implement a high-pass filter characteristic. However, the switched capacitor impedance formed by the input chopper and the input capacitance of the amplifier accentuates its low frequency noise. $C_1$ must be large, typically 300 pF, in order to mitigate low frequency noise but this has the disadvantage that it reduces the input impedance of the amplifier. A positive feedback loop can be used to boost the input impedance of the amplifier as will be described below.

Whilst the CMFB circuit 1080 can be implemented in different ways, a capacitive summing amplifier can be used as shown in FIG. 10. In FIG. 10, a capacitive summing amplifier 1110 is implemented as the CMFB circuit 1080 of FIG. 9. (Previously described components are not described again here.) The capacitive summing amplifier 1110 comprises eight low-pass filters (LPFs) 1120 connected to received respective ones of the output signals 1050, 1052, 1054, 1056, 1058, 1060, 1062, 1064 from respective ones of the active electrodes 1030, 1032, 1034, 1036, 1038, 1040, 1042, 1044. Each LPF 1120 is connected to a capacitor 1130. The LPFs 1120 and capacitors 1130 are connected in series and are connected to the inverting input of an amplifier 1150. Each capacitor 1130 effectively blocks any residual DC drift of the active electrode 1030, 1032, 1034, 1036, 1038, 1040, 1042, 1044 with which it is associated. This allows the amplifier 1110 to provide a stable reference voltage, $V_{ref}$, at the common non-inverting input 1085 thereof. The average CM of the eight channels is determined and multiplied by a factor that is the ratio of the channel capacitance to the feedback capacitance of the amplifier 1150.

FIG. 10 also shows further elements of each active electrode 1030, 1032, 1034, 1036, 1038, 1040, 1042, 1044, namely, the impedance boost loop 1190, a clock generation circuit 1160, and a bias generation circuit 1170. A ripple reduction loop 1080 and a DC servo loop 1085 are also shown, their operation being described below with reference to FIG. 17. Another bias generation circuit 1190 is also included in the back-end 1070.

Figure 11:
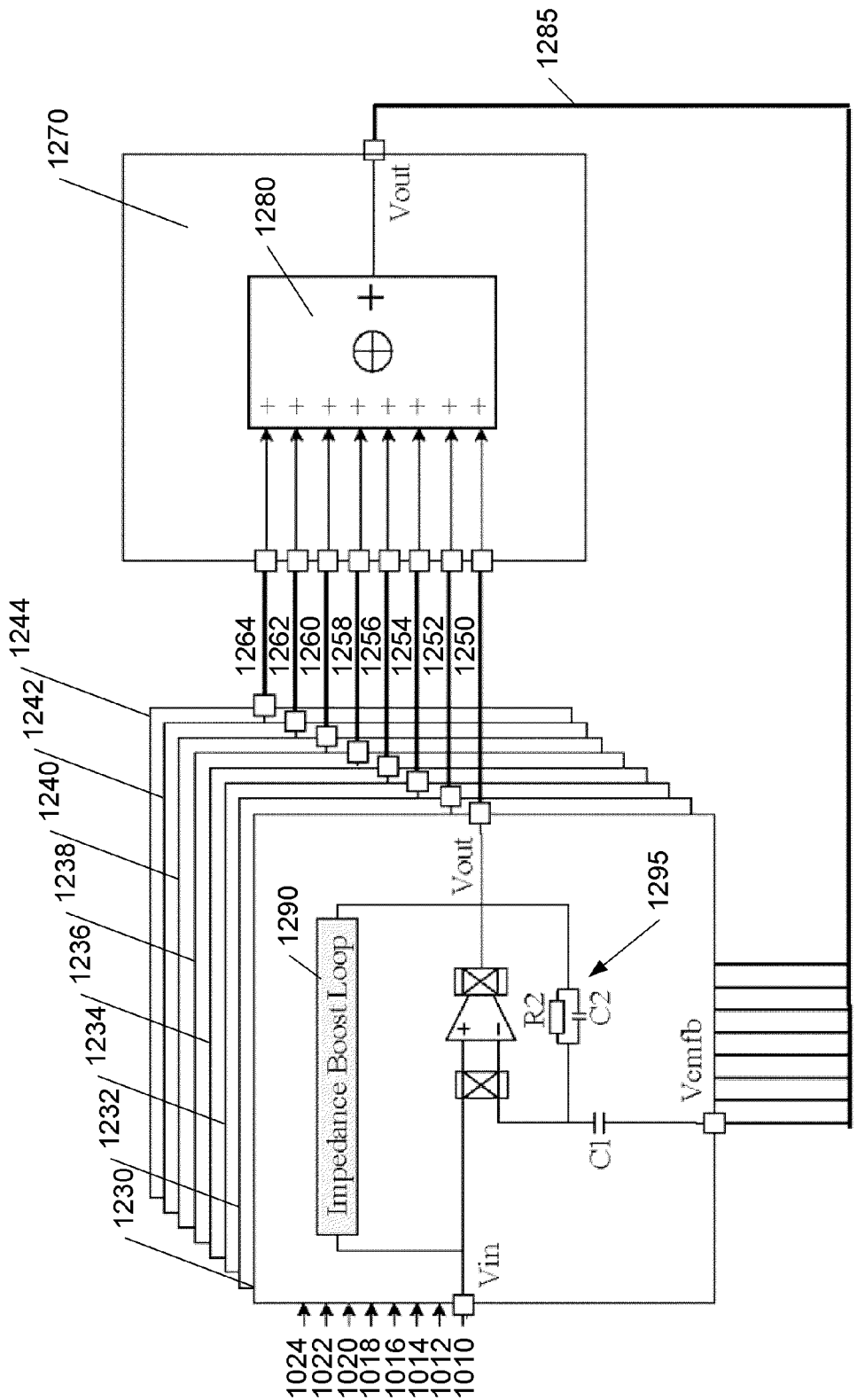
FIG. 11 is similar to FIG. 8 but for a system having a non-inverting amplifier and non-inverting CMFB circuit.

FIG. 11 is similar to FIG. 9 and illustrates an eight-channel active electrode system 1200 with non-inverting amplifier 1295 and non-inverting CMFB 1280. Eight input channels 1010, 1012, 1014, 1016, 1018, 1020, 1022, 1024 are input to respective active electrodes 1230, 1232, 1234, 1236, 1238, 1240, 1242, 1244 as shown. Eight output signals 1250, 1252, 1254, 1256, 1258, 1260, 1262, 1264 from respective ones of the active electrodes 1230, 1232, 1234, 1236, 1238, 1240, 1242, 1244 are input to a back-end 1270. The back-end 1270 comprises a non-inverting CMFB circuit 1280 that provides an output 1285 that is fed back to each of the active electrodes 1230, 1232, 1234, 1236, 1238, 1240, 1242, 1244 as shown.

Each active electrode 1230, 1232, 1234, 1236, 1238, 1240, 1242, 1244 includes an impedance boost circuit 1290 with a non-inverting amplifier arrangement 1295 as will be described in more detail below.

Figure 12:
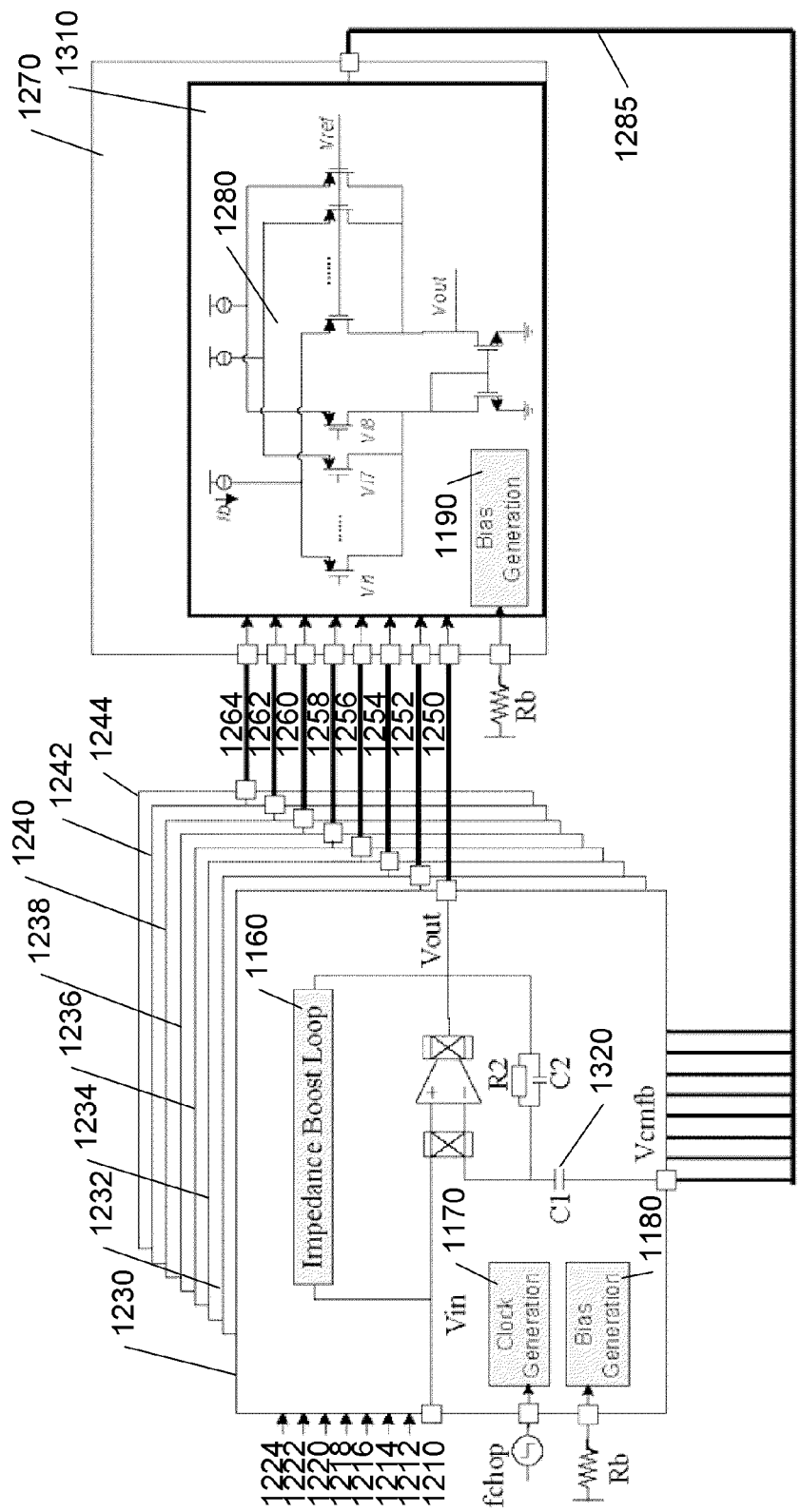
FIG. 12 is similar to FIG. 11 but illustrating a possible implementation of the non-inverting CMFB circuit.

Again, whilst the CMFB circuit 1280 can be implemented in different ways, an open-loop voltage summing amplifier is used as shown in FIG. 12. In FIG. 12, an open-loop voltage summing amplifier 1310 is implemented as the CMFB circuit 1280 of FIG. 11. The open loop voltage amplifier 1310 is not AC-coupled as required for an inverting active electrode. This is because the inverting active electrode needs the input bias voltage, $V_{ref}$, at the input and capacitor 1320 of the non-inverting amplifier arrangement 1295 blocks any DC drift from the CMFB circuit 1270.

FIG. 12 also shows further elements of each active electrode 1230, 1232, 1234, 1236, 1238, 1240, 1242, 1244, namely, an impedance boost loop 1160, a clock generation circuit 1170, and a bias generation circuit 1180. Another bias generation circuit 1190 is also included in the back-end 1270. In order to improve the CMRR between the active electrodes 1230, 1232, 1234, 1236, 1238, 1240, 1242, 1244, the CM inputs for inputs 1210, 1212, 1214, 1216, 1218, 1220, 1222, 1224 of all active electrodes 1230, 1232, 1234, 1236, 1238, 1240, 1242, 1244 are fed forward through capacitor 1320 of each active electrode to the common reference node 1285. Therefore, the CM output voltage at 1250, 1252, 1254, 1256, 1258, 1260, 1262, 1264 are minimized because there is no CM current passing through capacitor 1320.

Figure 13:
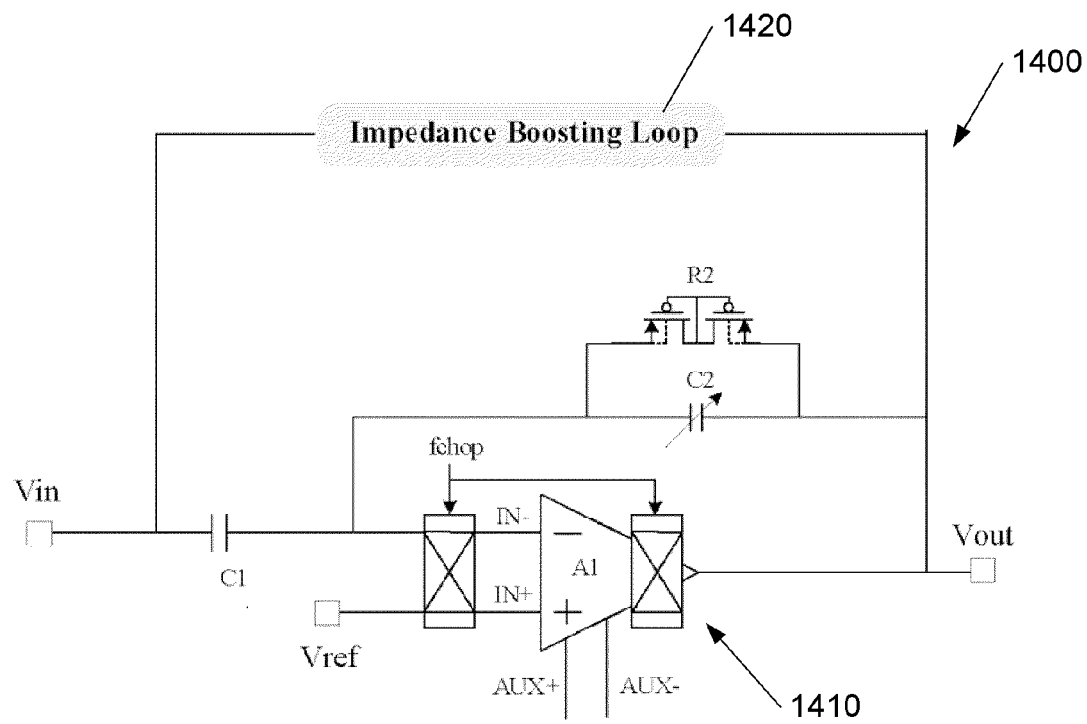
FIG. 13 is a schematic illustration of the implementation of an inverting amplifier in the active electrode in accordance with one embodiment.

FIG. 13 illustrates an active electrode 1400 that is implemented as an inverting amplifier 1410. The amplifier 1410 is shown with an impedance boosting loop 1420 which will be described in more detail below.

Figure 14:
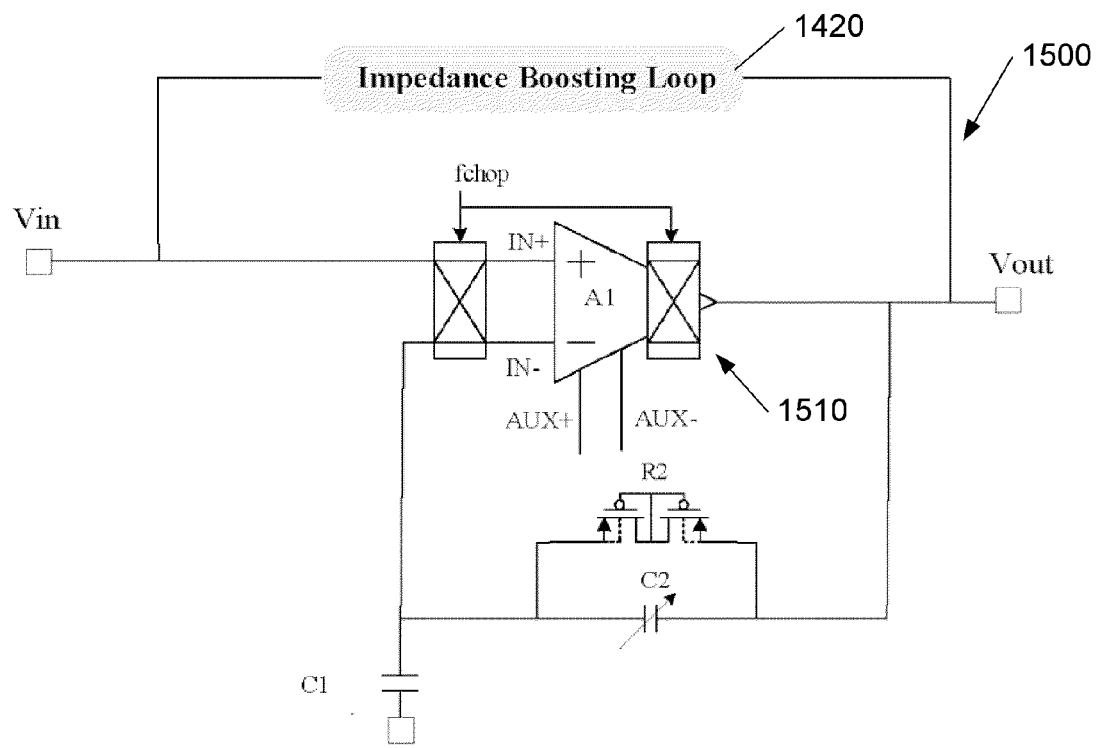
FIG. 14 is a schematic illustration of the implementation of a non-inverting amplifier in the active electrode in accordance with one embodiment.

Similarly, in FIG. 14, an active electrode 1500 is shown that is implemented as a non-inverting amplifier 1510. The amplifier 1510 is with the impedance boosting loop 1420.

Figure 15:
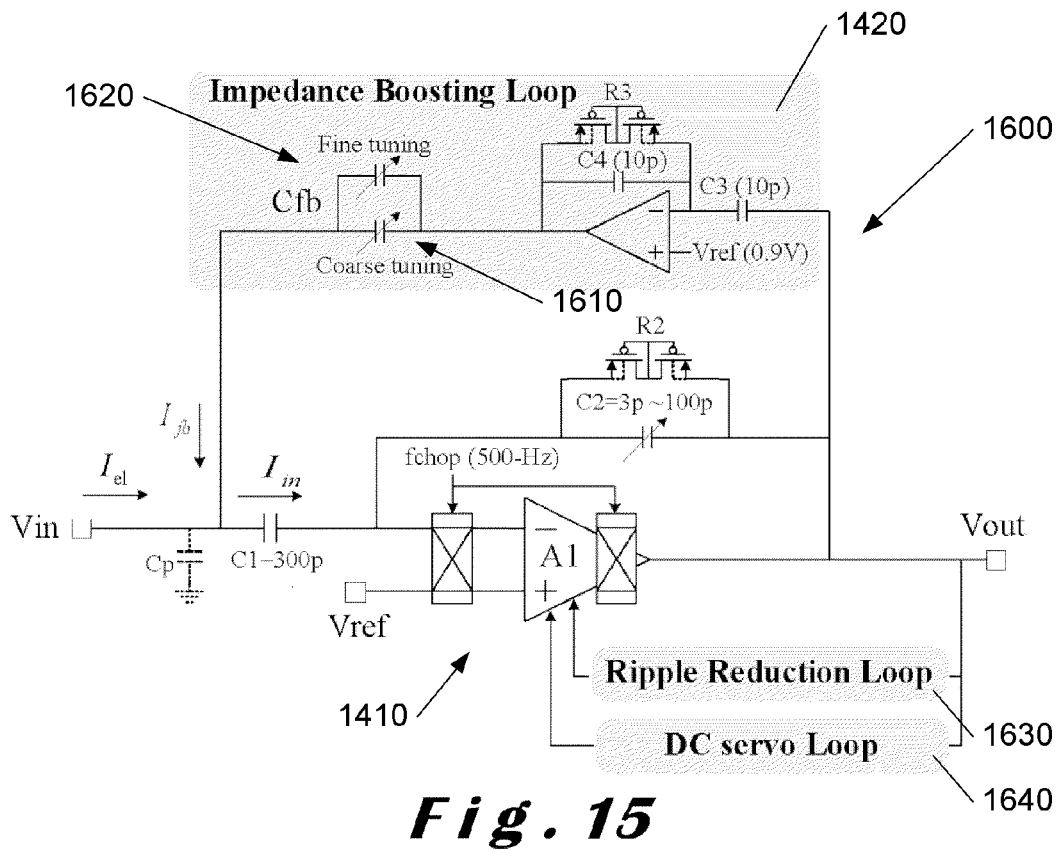
FIG. 15 illustrates on implementation of an impedance boost loop of FIGS. 13 and 14.

FIG. 15 illustrates an active electrode 1600 in more detail. The active electrode 1600 is similar to that of FIG. 13 but with the impedance boosting loop 1420 shown in more detail. The impedance boosting loop 1420 supplies part of the input current, $I_{in}$, through capacitor, $C_1$, as shown. This reduces the current that is drawn from the recording electrode, $I_{el}$. The impedance boosting loop 1420 comprises a feedback capacitance that provides a feedback current, $I_{fb}$, that adds to the recording electrode current, $I_{el}$. The feedback current, $I_{fb}$, is determined by a combination of a coarse capacitor array 1610 and a fine capacitor array 1620. At various gain settings, the capacitors of the coarse array 1610 are switched in tandem with the value of the variable capacitor, $C_2$. The fine array 1620 can then be adjusted to compensate for the current that flows into the bond-pad and other parasitic capacitances. In addition, active electrode 1600 includes two further feedback loops 1630, 1640 that reduce the effects of output ripple and residual offset. Both these loops are shown in more detail in FIG. 16.

Figure 16:
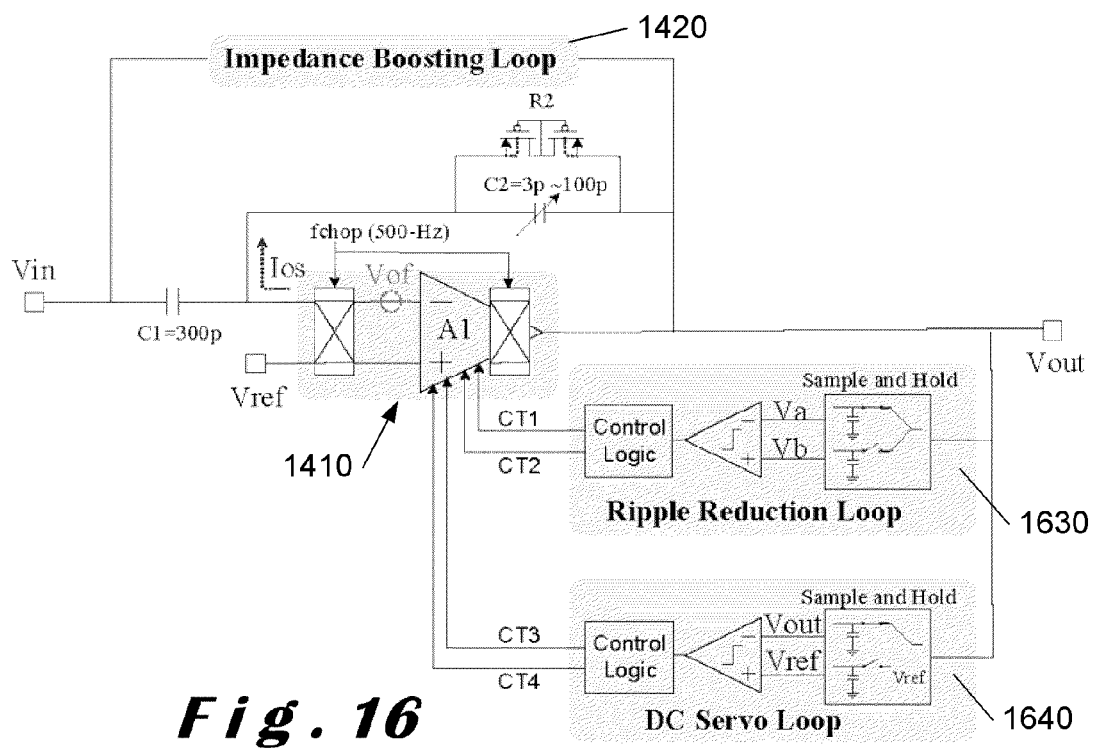
FIG. 16 is a schematic illustration of a current-DAC based offset calibration circuit in accordance with one embodiment.

FIG. 16 is similar to FIG. 15 but shows the two further feedback loops 1630, 1640 in more detail. Here, a ripple reduction loop (RRL) 1630 and a DC servo loop (DSL) 1640 are shown. These two loops 1630, 1640 are intended to compensate for chopper-stabilized amplifier associated offsets. Both the RRL 1630 and the DSL 1640 are digitally-assisted calibration loops that exploit the fact that ripple and offset are relatively static and do not need to be continuously reduced. Calibration starts with the RRL 1630. Peak ripple levels, $V_a$ and $V_b$, are synchronously sampled and their polarity is determined by a comparator (not shown). A logic circuit, implementing the SAR algorithm, sets the input to a 7-bit current DAC in seven clock cycles. The DAC is implemented by two current mirror arrays (not shown) within the amplifier 1410. The DSL 1640 operates in a similar manner as it samples the output voltage, $V_{out}$, and compares it to the reference voltage, $V_{ref}$, to set the input to another pair of current DACs within the amplifier 1410. Their outputs are chopped in order to generate a modulated compensation current. Once the calibration is finished, the inputs to the current DACs are frozen and the RRL 1630 and DSL 1640 are shut down to allow normal signal amplification. The power dissipation of the RRL 1630 and the DSL 1640 is determined by the DAC currents and is less than about 400 nW.

Although the ripple reduction loop and the DC servo loop have been described with reference to their use with an inverting active electrode in FIGS. 15 and 16, it will readily be appreciated that both loops can also be implemented with a non-inverting active electrode.

The front- and back-end of an eight-channel active electrode system can be implemented in a standard 0.18 μm CMOS process and consumes a total of 160 μW from a 1.8V supply. Measurement results are shown in FIGS. 17 to 20.

Figure 17:
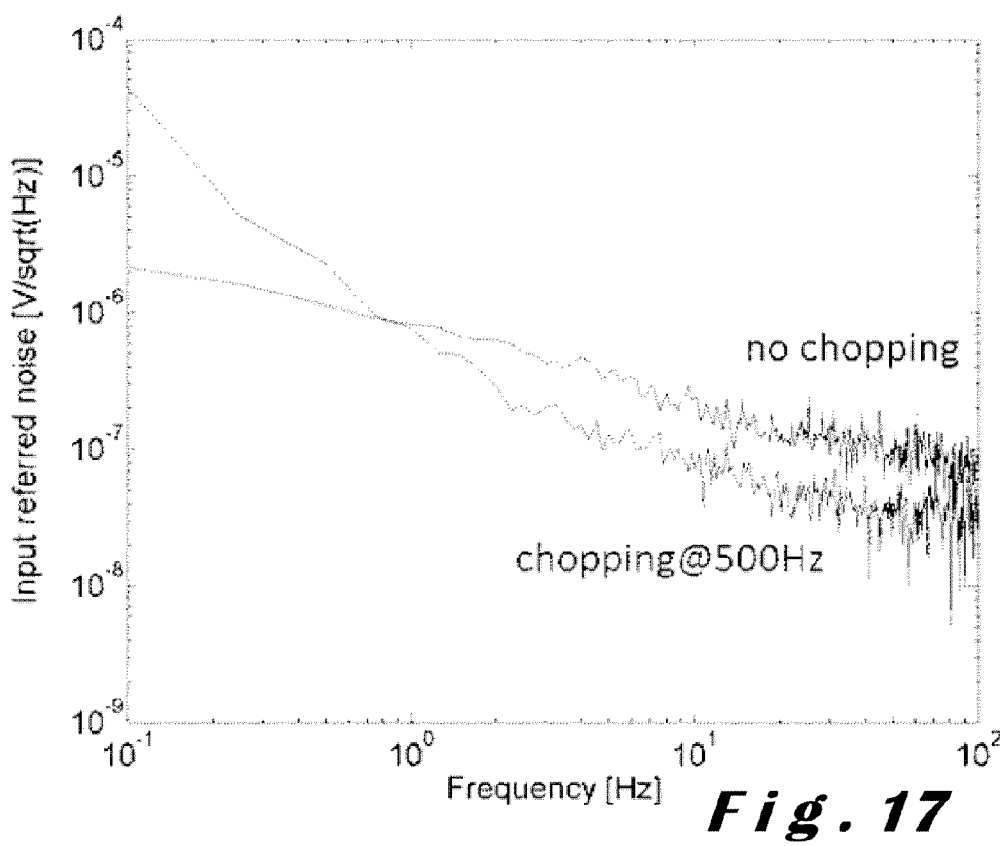
FIG. 17 is a graph illustrating the effect of chopping.
Figure 18:
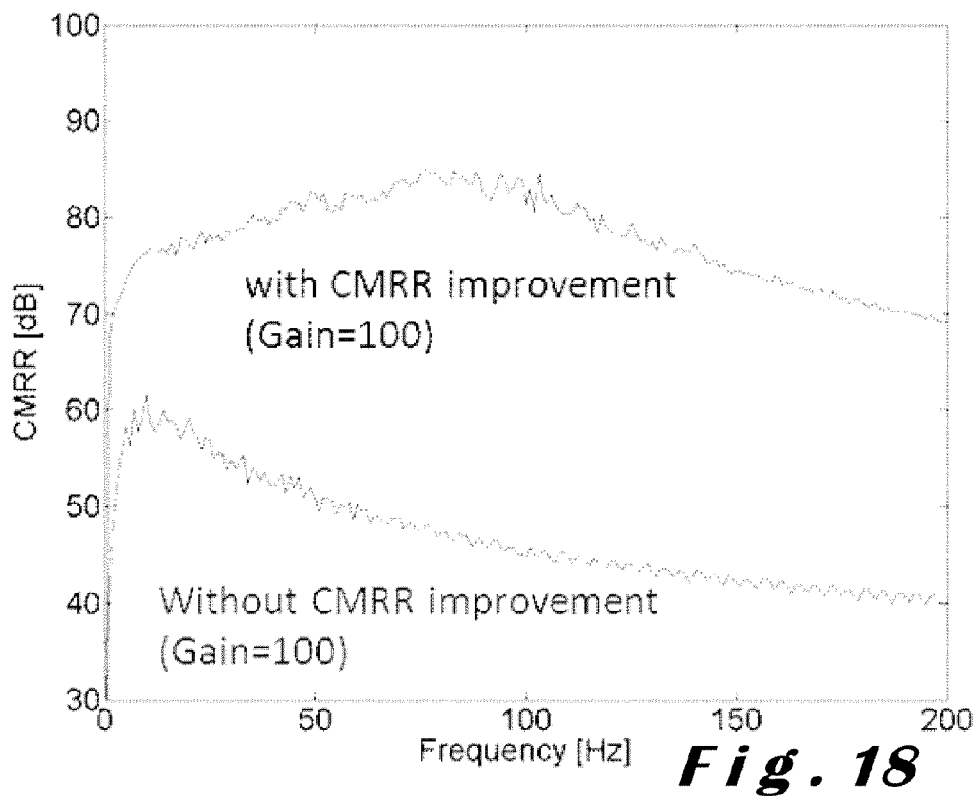
FIG. 18 is a graph illustrating CMRR improvement.
Figure 19:
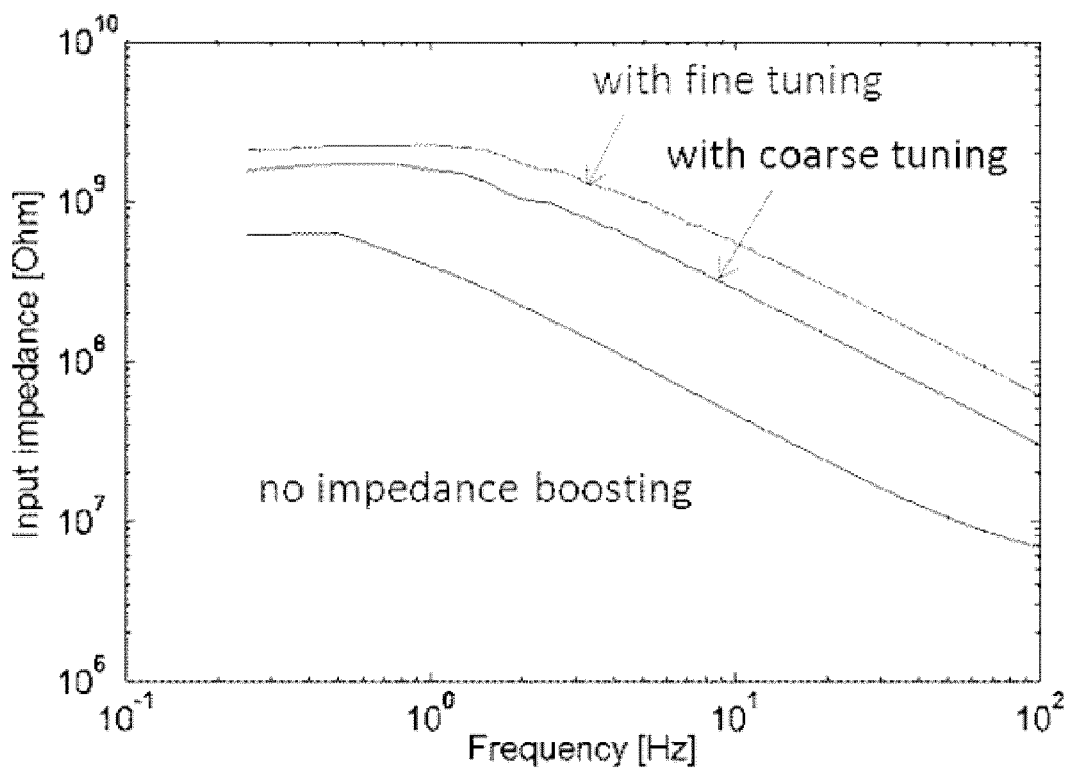
FIG. 19 is a graph illustrating the effect of impedance boosting for both coarse and fine tuning.
Figure 20:
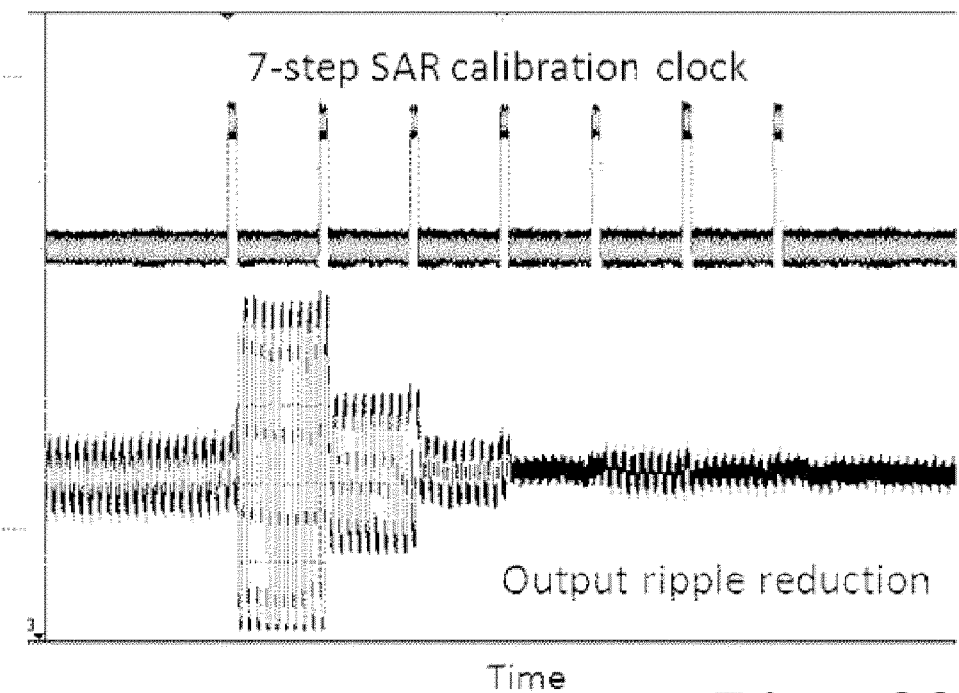
FIG. 20 is a graph illustrating output ripple reduction.

FIG. 17 illustrates the noise of the amplifier with and without chopping. Chopping at 500 Hz leads to a total input referred noise of 0.8 $\mu V_{rms}$ for a frequency range of between 0.5 Hz to 100 Hz. FIG. 18 illustrates that at 50 Hz the back-end CMFB improves the CMRR by between 35 dB to 82 dB. FIG. 19 illustrates the effect of a 2GΩ impedance achieved by the impedance boosting loop. FIG. 20 illustrates that the RRL reduced the output ripple from 40 mV to 2 mV. Although not shown, the DSL reduced the output drift from 280 mV to 20 mV.

As described above, a biopotential acquisition system in accordance with one embodiment is realized through the use of an AC coupled chopper-stabilized amplifier in conjunction with back-end CM feedback, input impedance boosting and digital offset calibration. Such a system well suited for gel-free active electrode applications. Its performance was found to exceed state-of-the-art in terms of its CMRR, input impedance, offset rejection and power-efficient offset compensation.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A system for acquiring biopotential signals of a user, the system comprising:
   at least two biopotential channels, each channel comprising an electrode configured to detect a biopotential input signal and an amplifier configured to amplify the biopotential input signal to provide an amplified biopotential output signal, at least one of the biopotential channels comprising an active electrode formed by the electrode and the amplifier, each amplifier in each active electrode comprising a chopper-stabilized capacitively-coupled amplifier;
   a back-end processing circuit configured to process the amplified biopotential output signals; and
   a common-mode feedback system connected to receive the amplified biopotential output signals to determine an average common-mode signal from the amplified biopotential output signals, the system being further configured to feed the average common-mode signal back to each amplifier to enhance common-mode rejection ratio of the system.

2. The system according to claim 1, further comprising a plurality of biopotential channels, each biopotential channel comprising an active electrode, the average common-mode signal being fed back to an input of each amplifier.

3. The system according to claim 2, wherein the common-mode feedback system comprises an inverting common-mode feedback system and each active electrode comprises an inverting amplifier.

4. The system according to claim 3, wherein the average common-mode signal is fed back to the non-inverting input of the amplifier.

5. The system according to claim 3, wherein the inverting common-mode feedback system comprises a capacitive summing amplifier.

6. The system according to claim 2, wherein the common-mode feedback system comprises a non-inverting common-mode feedback system and each active electrode comprises a non-inverting amplifier.

7. The system according to claim 6, wherein the common-mode signal is fed back to the inverting input of the amplifier.

8. The system according to claim 6, wherein the non-inverting common-mode feedback system comprises an open-loop voltage summing amplifier.

9. The system according to claim 2, wherein each active electrode comprises an impedance boost loop.

10. The system according to claim 2, wherein each active electrode comprises a ripple reduction loop.

11. The system according to claim 2, wherein each active electrode comprises a DC servo loop.

12. The system according to claim 2, wherein the common-mode feedback system forms part of the back-end processing circuit.

13. The system according to claim 1, wherein the back-end processing circuit comprises a further amplifier and an analogue-to-digital converter.

14. A system for acquiring biopotential signals of a user, the system comprising:
   at least two biopotential channels, each channel comprising an electrode configured to generate a biopotential input signal and an amplifier configured to amplify the biopotential input signal, each amplifier comprising a chopper-stabilized capacitively-coupled amplifier; and
   a common-mode feedback system connected to receive the amplified biopotential output signals to determine an average common-mode signal from the amplified biopotential output signals and to feed the average common-mode signal back to each of the amplifiers to enhance common-mode rejection ratio of the system.

15. The system according to claim 14, further comprising a back-end processing circuit configured to process the amplified output signals, wherein the back-end processing circuit comprises a further amplifier and an analogue-to-digital converter.

16. The system according to claim 14, wherein at least one of the biopotential channels comprises an active electrode formed by its electrode and the amplifier.

17. The system according to claim 16, further comprising a plurality of biopotential channels, each biopotential channel comprising an active electrode, the average common-mode signal being fed back to an input of each amplifier.

18. A system for acquiring biopotential signals of a user, the system comprising:
   at least two biopotential channels, each channel comprising an electrode configured to generate a biopotential input signal and an amplifier configured to amplify the biopotential input signal, each amplifier comprising a chopper-stabilized capacitively-coupled amplifier;
   means for processing the amplified biopotential output signals; and
   means for receiving the amplified biopotential output signals to determine an average common-mode signal from the amplified biopotential output signals and for feeding the average common-mode signal back to each of the amplifiers to enhance common-mode rejection ratio of the system.

* * * * *